US007042565B2

(12) United States Patent
Wang et al.

(10) Patent No.: US 7,042,565 B2
(45) Date of Patent: May 9, 2006

(54) FLUORESCENT MICROARRAY ANALYZER

(75) Inventors: Jiann-Hua Wang, Taipei (TW); Hui Ju Chen, Tainan (TW); Tzu-Chiang Wu, Miaoli (TW); Chien-Ho Chuang, Kaohsiung (TW); Tsung-Kai Chuang, Tainan (TW)

(73) Assignee: Kaiwood Technology Co., Ltd., Tainan (TW)

( * ) Notice: Subject to any disclaimer, the term of this patent is extended or adjusted under 35 U.S.C. 154(b) by 47 days.

(21) Appl. No.: 10/777,720

(22) Filed: Feb. 13, 2004

(65) Prior Publication Data

US 2005/0179894 A1 Aug. 18, 2005

(51) Int. Cl.
*G01N 21/64* (2006.01)
(52) U.S. Cl. .................................... 356/317; 250/458.1
(58) Field of Classification Search ................ 356/319, 356/317, 318, 417; 250/458.1, 459.1, 461.1, 250/461.2
See application file for complete search history.

(56) References Cited

U.S. PATENT DOCUMENTS 6,664,061 B1 * 12/2003 Elghanian et al. ............. 435/6

2004/0072722 A1 * 4/2004 Kornblith et al. ............... 514/1
2004/0265905 A1 * 12/2004 Chen et al. .................. 435/7.1

* cited by examiner

*Primary Examiner*—F. L. Evans
(74) *Attorney, Agent, or Firm*—Birch, Stewart, Kolasch & Birch, LLP

(57) ABSTRACT

A fluorescent microarray analyzer includes a light source for emitting a light beam, a light processing unit for focusing the light beam on the biochip and exciting fluorescent targets on the biochip to produce fluorescence, a focusing lens for focusing the fluorescence on a spectrophotometer, a spectrophotometer for detecting signal of the fluorescence, and an output device for selectively outputting/displaying the signal detected by the spectrophotometer. The resulting signal of the output device does not need to be converted into image data for analysis. For acquiring a more accurate result of detection of signal of fluorescence from the fluorescent targets, the photomultiplier tube of the conventional biochip scanner device is replaced with the spectrophotometer of fluorescent microarray analyzer of the present invention and the filter is removed. Without converting the signal into an image, no errors arise as what happened in process of converting an electrical signal into image data in the conventional biochip. Also, a real-time analysis of the signal proceeds while scanning samples on the biochip.

13 Claims, 6 Drawing Sheets

FLUORESCENT MICROARRAY ANALYZER

BACKGROUND OF THE INVENTION

1. Field of the Invention

The present invention relates to a fluorescent microarray analyzer, particularly to a fluorescent microarray analyzer for detecting fluorescent signals emitting from a biochip by means of spectrum analysis.

2. The Prior Arts

As "working draft" of the human sequence unraveled by the Human Genome Project published in Nature (15 Feb., 2001), simultaneously with a companion publication of the human sequence generated by Celera Genomics Corporation (Science, 16 Feb., 2001), understanding the physical functions and the mechanisms of human genes becomes the next important goal in the field. To accelerate the progress of the related research, high-throughput tools for efficient analysis are available. Biochip, results of mass of samples expressed on surface of a small solid carrier, is such a useful analytic tool. Biochip can be employed in gene expression, drug selection and disease diagnosis in both basic research and clinical application fields.

Three kinds of biochips are known, namely DNA chip, lab-on-a-chip and protein chip. Since the protein chip and the lab-on-a-chip are difficult to operate, the DNA chip is in common use now. The detection of the DNA chip is shown in FIG. 1. Known DNA fragments serving as DNA probes (2) are immobilized onto a surface of a glass slide or a silicon chip and form a DNA chip (1). Generally, the DNA probes (2) are arranged in array, which is called DNA microarray. On the other hand, unknown DNA fragments (3), the target DNA, are labeled with fluorescent dyes. The DNA chip (1) is then hybridized with the target DNA (3). After washing, only DNA fragments hybridized with DNA probes are left on the DNA chip (1). By scanning with a biochip reader, the fluorescence from the fluorophores on the slide is detected and the obtained hybridization result is analyzed.

FIG. 2 is a schematic view showing a conventional biochip reader (4). Beams of light emitted from a laser source (40) pass through a focusing lens (41), reflected by a beam splitter (42), and then further passing through another focusing lens (43) to irradiate a surface of the biochip (44). The fluorescent dyes on the biochip (44) are excited by the beams of light and in turn emits fluorescence (45). The fluorescence (45) passes through the focusing lens (43), the beam splitter (42), and the focusing lens (46). The fluorescence (45) further passes through a filter (47) and with which the beams of light from the light source are filtered out. The fluorescence is then detected by a photomultiplier tube (PMT) (48), which converts the optic signals into electrical signals, which are fed to a computer (49) and processed to form image data. In the conventional biochip reader, to obtain the final result requires scanning all samples on the biochip, converting optic signals into electrical signals, and forming the electrical signal image data for analysis. The conventional biochip is disadvantageous, since errors occur in the formation of the image data by processing the electrical signal and it takes much time to obtain the image.

Cyanine 3 (Cy3) and cyanine 5 (Cy5) are two fluorophores in common use. Cy3, with peak absorption at 550 nm, is generally excited with a laser beam of 532 nm and emitting fluorescence which has central wavelength at 570 nm. Cy5, with peak absorption at 649 nm, is generally excited with laser beams of 632.8 nm or 635 nm and emitting fluorescence which has central wavelength at 678 nm. Filters are generally used to eliminate the interference caused by the original beams of light from the light source and the scattering light from the slide. When filtering out the interfering light from the light source, some signals of the resulting fluorescence may be filtered out at the same time due to the crosstalk between the fluorescence and the interfering light. In addition, problems of exchanging filters happens when two or more fluorophores are used on the same biochip.

SUMMARY OF THE INVENTION

A primary object of the present invention is to provide a fluorescent microarray analyzer in which the photomultiplier tube of the conventional biochip scanner device is replaced with a spectrophotometer. Therefore, accurate signals of fluorescence are obtained, and there is no need to set a filter.

A second object of the invention is to provide a fluorescent microarray analyzer that allows for real-time analysis without scanning all samples on the biochip. As a result, a lot of time taken for analysis is saved.

A third object of the invention is to provide a fluorescent microarray analyzer that reads signals from spectrophotometer directly without conversion into image data and thus eliminating errors occurring during the conversion.

In order to realize the foregoing objects, a fluorescent microarray analyzer of the present invention comprises: a light source for emitting light beam; a light processing unit for focusing the beams on the biochip and exciting fluorescent targets on the biochip to produce fluorescence; a focusing lens for focusing the fluorescence on a spectrophotometer, which detects the fluorescence; and an output device for outputting/displaying the signal detected by the spectrophotometer. The resulting signal of the output device is not a converted image data. The light processing unit comprises: a beam splitter for reflecting the light beam to pass through a focusing lens which focuses the light beam on the biochip and exciting fluorescent targets on the biochip to produce fluorescence which passes through the beam splitter and the focus lens to the spectrometer. Another focusing lens may be set between the light source and the beam splitter to enhance the focusing effect.

Furthermore, if desired, image data can be produced by conversion from the signals detected by the spectrophotometer. The image data are used for showing the positions of DNA spots on a biochip. The signal intensity of each sample comes from the signals detected by the spectrophotometer and therefore no errors arise as what happened in the process of converting an electrical signal into an image data in the conventional biochips.

The resulting signals of fluorescence are obtained by the spectrophotometer of the present invention. A real-time analysis proceeds while samples on the biochip are being scanned. As signals of different wavelength can be shown by the spectrophotometer, a more accurate result of signals of fluorescence form samples is obtained without a filter. In addition, more accurate results are produced even more than two fluorophores are used on the same biochip.

For more detailed information regarding advantages and features of the present invention, examples of preferred embodiments will be described below with reference to the annexed drawings. It is to be understood that both the foregoing general description and the following detailed description are exemplary and explanatory and are intended to provide further explanation of the invention as claimed.

BRIEF DESCRIPTION OF THE DRAWINGS

The related drawings in connection with the detailed description of the present invention to be made later are described briefly as follows, in which.

DETAILED DESCRIPTION OF THE PREFERRED EMBODIMENT

Figure 1:
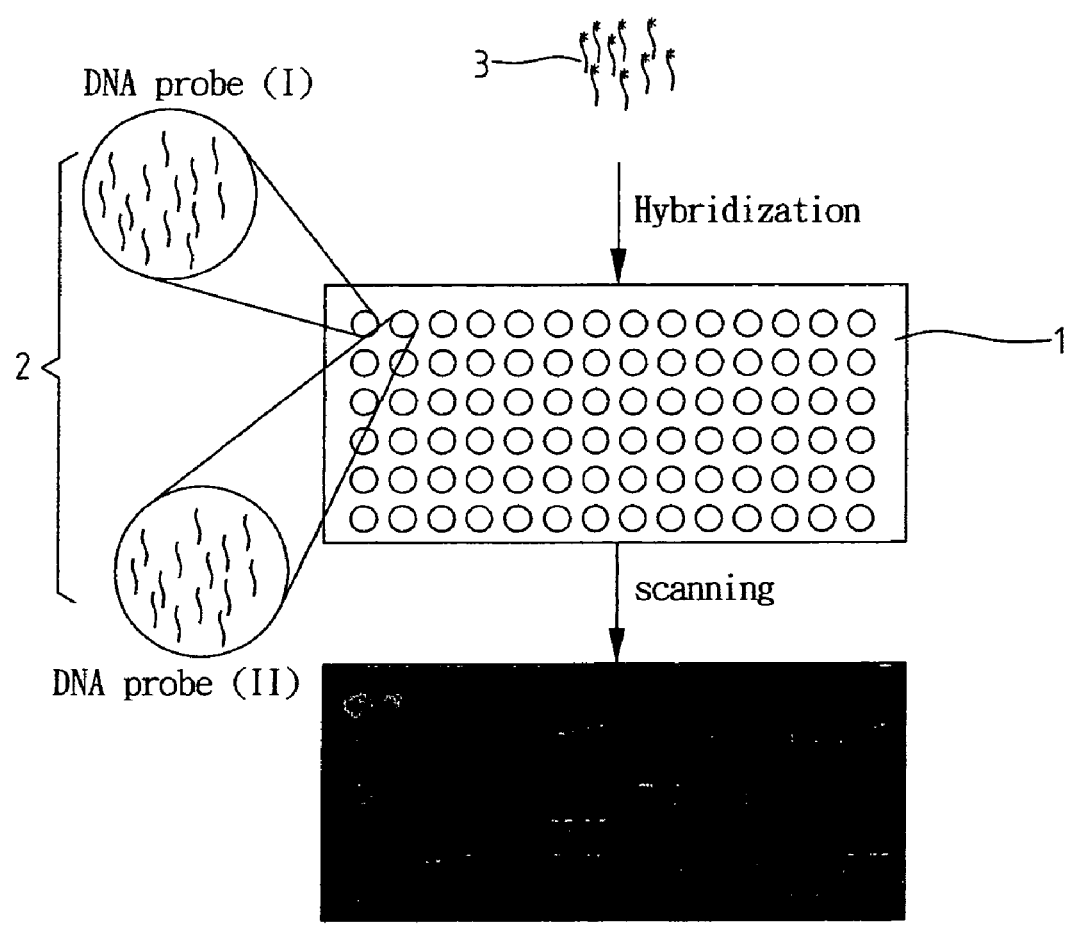
FIG. 1 illustrates a conventional DNA chip detection system.
Figure 2:
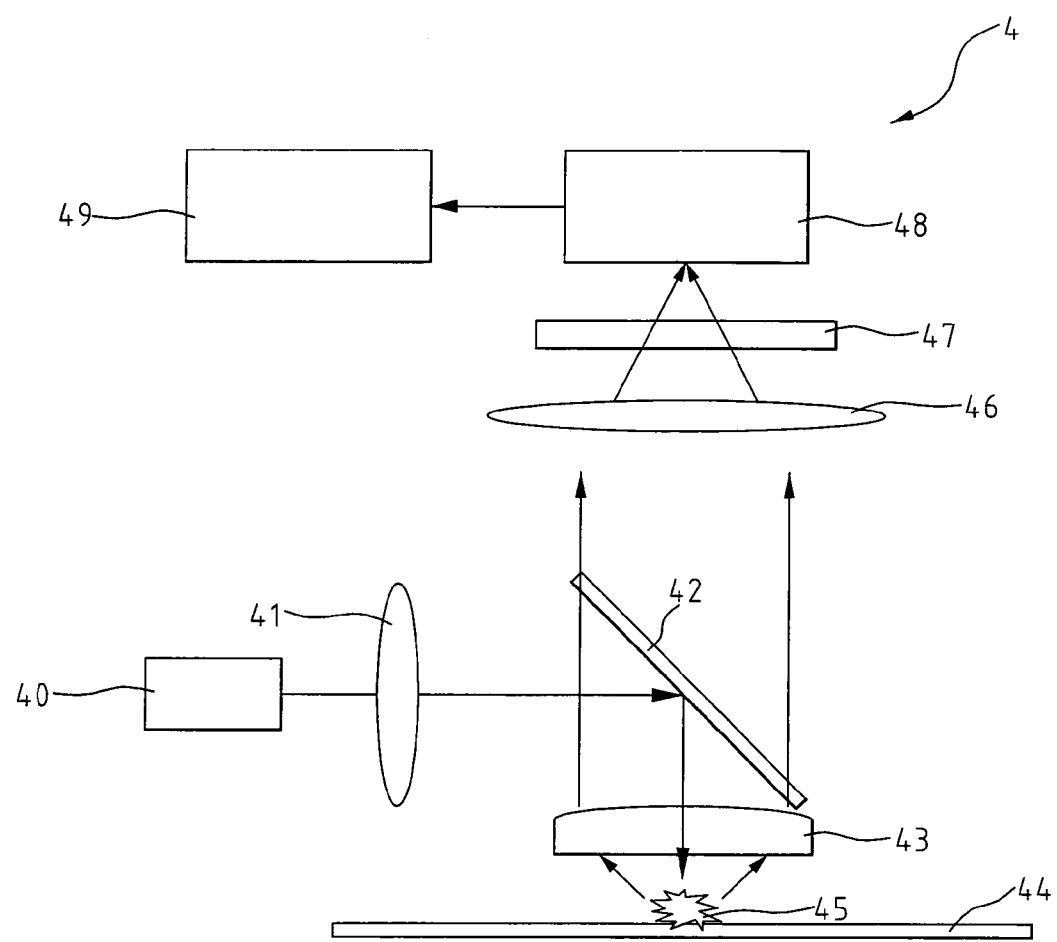
FIG. 2 is a schematic view showing an example of a conventional biochip reader.
Figure 3:
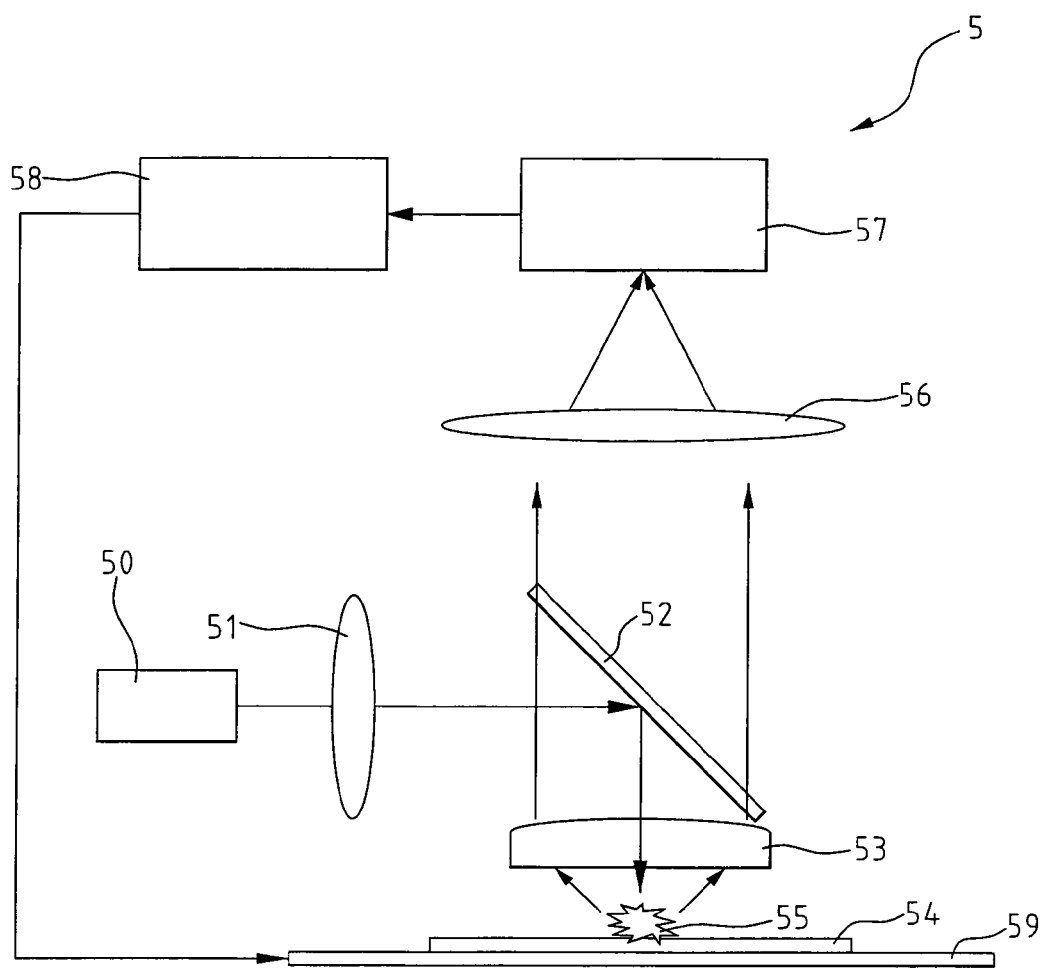
FIG. 3 is a schematic view showing an embodiment of the fluorescent microarray analyzer of the present invention.

Preferred embodiments of the present invention will now be described in detail below with reference to the accompanying drawings. FIG. 3 is a schematic view showing an embodiment of a fluorescent microarray analyzer (5) of the present invention. The fluorescent microarray analyzer (5) comprises a light source (50) for emitting light beam; a beam splitter (52) for redirecting the light beam through a focusing lens (53), which focuses the reflected light beam onto a biochip (54) and exciting fluorescent targets on the biochip (54) to produce fluorescence (55); a focusing lens (56) for focusing the fluorescence on a spectrophotometer; a spectrophotometer (57) for detecting the fluorescence; and an output device (58) for receiving and displaying the signal detected by the spectrophotometer. A further focusing lens (51) may be set between the light source (50) and the beam splitter (52) to enhance the focusing effect.

A biochip is placed on a platform (59) first when analyzed by the fluorescent microarray analyzer of the present invention. The platform (59) is movable in two different directions, for example X and Y directions that are orthogonal, under the control of a computer (58). When scanning, the light beam from laser source (50) passes through the focusing lens (51) and reaches a surface of the biochip (54). Fluorescence (55) is excited from fluorescent targets on the biochip (54). The fluorescence (55) passes through the focusing lens (53), the beam splitter (52) and the focusing lens (56) to focus on the spectrophotometer (57). The signal of fluorescence is detected by the spectrophotometer (57) and transmitted to an output device (58). The signal is output/displayed directly by the output device (58). For the convenience of analysis, the output device (58) may comprise a computer, which is loaded with a algorithm to control the movement of the platform (59) so that operation of the fluorescent microarray analyzer (5) is more easily.

Figure 4:
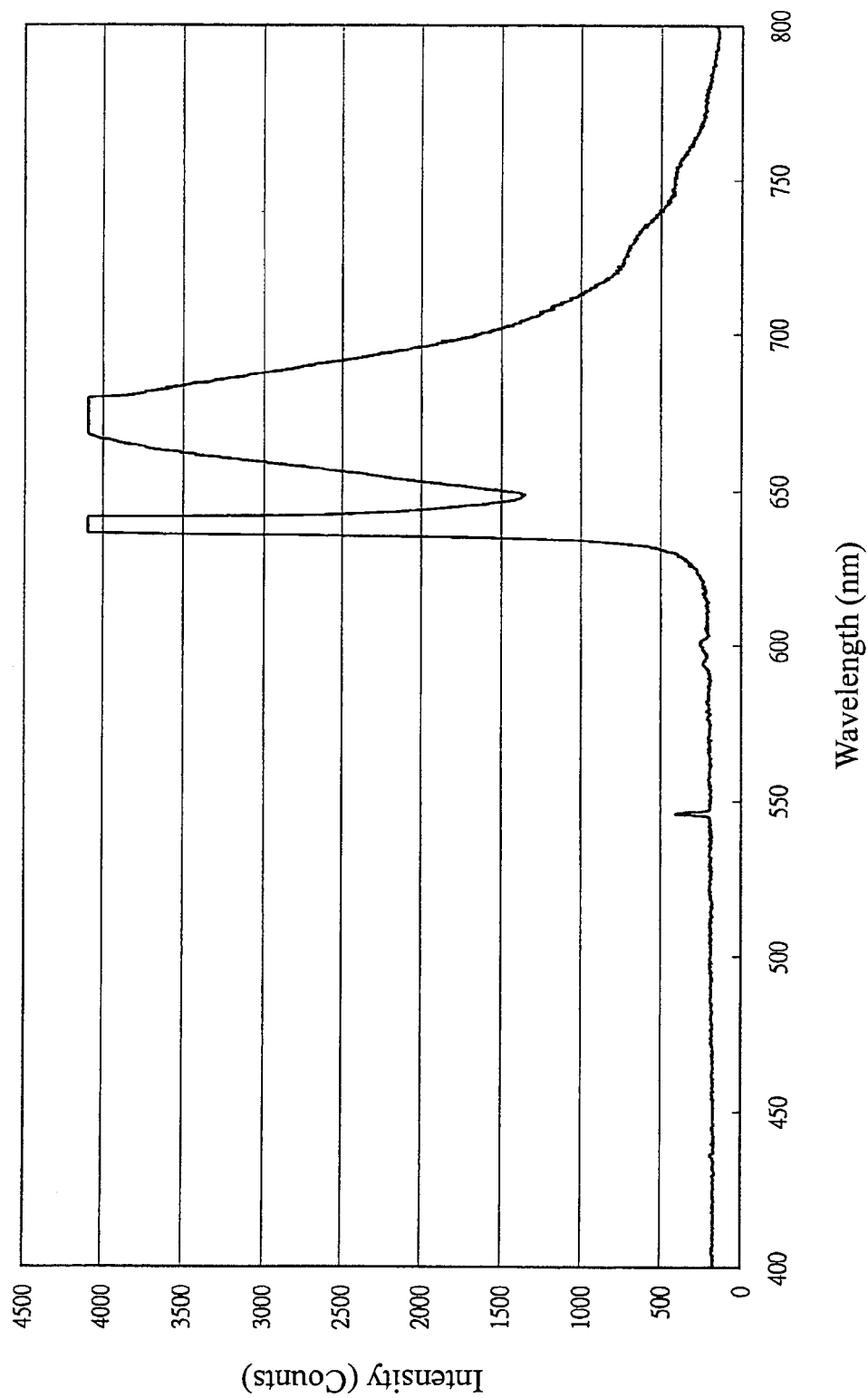
FIG. 4 is a spectrum analysis curve of Cy5 obtained by the fluorescent microarray analyzer of the present invention.

FIG. 4 is a spectrum analysis curve of Cy5 obtained by the fluorescent microarray analyzer of the present invention. The curve as shown is the result of a single sample, in which the laser's wavelength at 635 nm and the central peak of the emitted fluorescence at 678 nm are clearly distinguished. The signals of fluorescence are clear and are not interfered without a filter.

Figure 5:
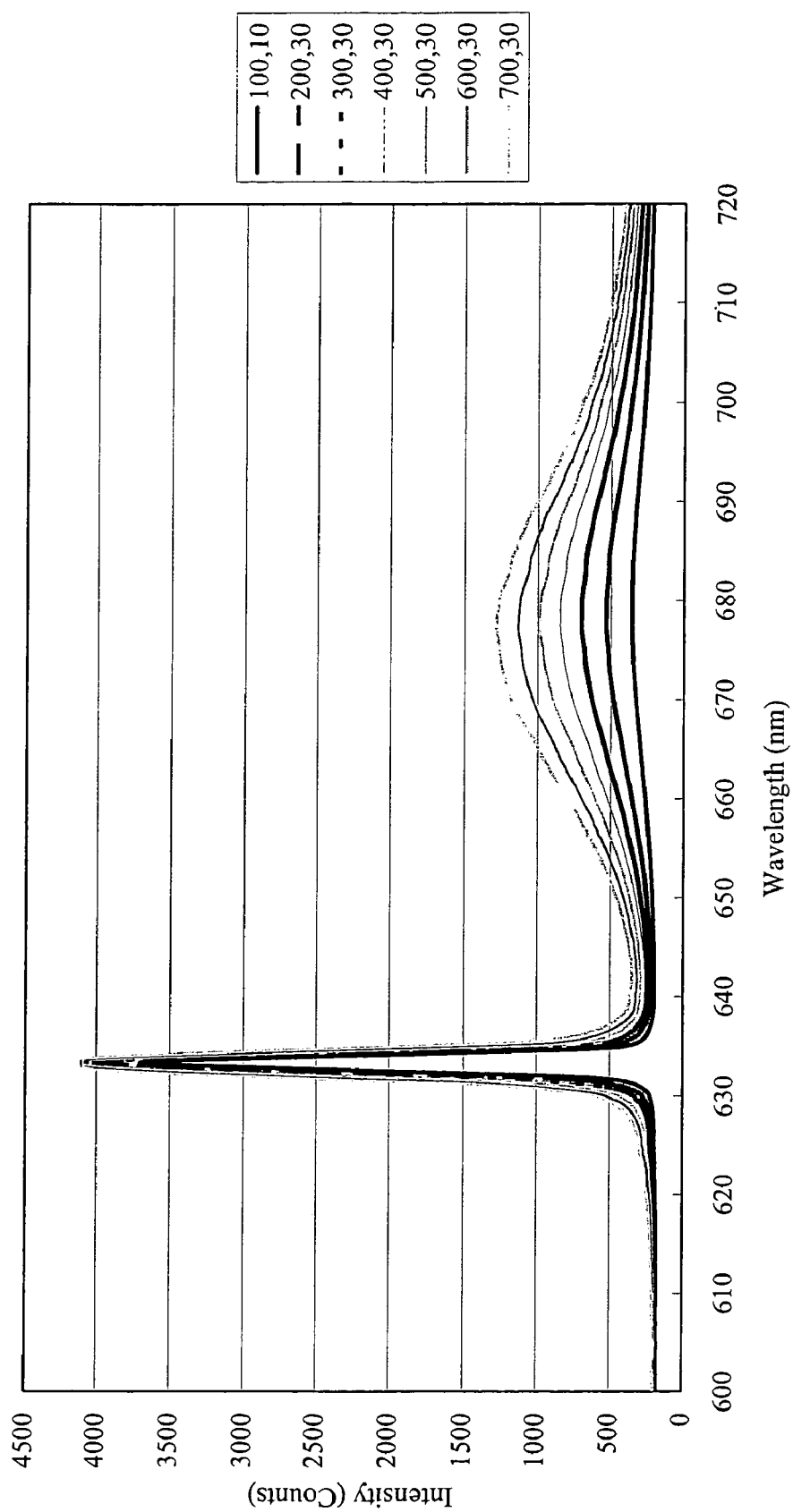
FIG. 5 is a spectrum analysis result of Cy5 obtained at different signal accumulation time by the fluorescent microarray analyzer of the present invention.

If the concentration of the sample is lower and the emitting fluorescence is weaker, detection time can be extended, as shown in FIG. 5. To obtain a more intensive signal, data is recorded after accumulating sufficient fluorescence. FIG. 5 is a spectrum analysis result of Cy5 obtained at different signal accumulation time (from 100 seconds to 700 seconds) by the fluorescent microarray analyzer of the present invention. As the signal accumulation time increases, the value of the signal increases. As a result, the weaker signal is acquired and analytic sensitivity is increased.

Figure 6:
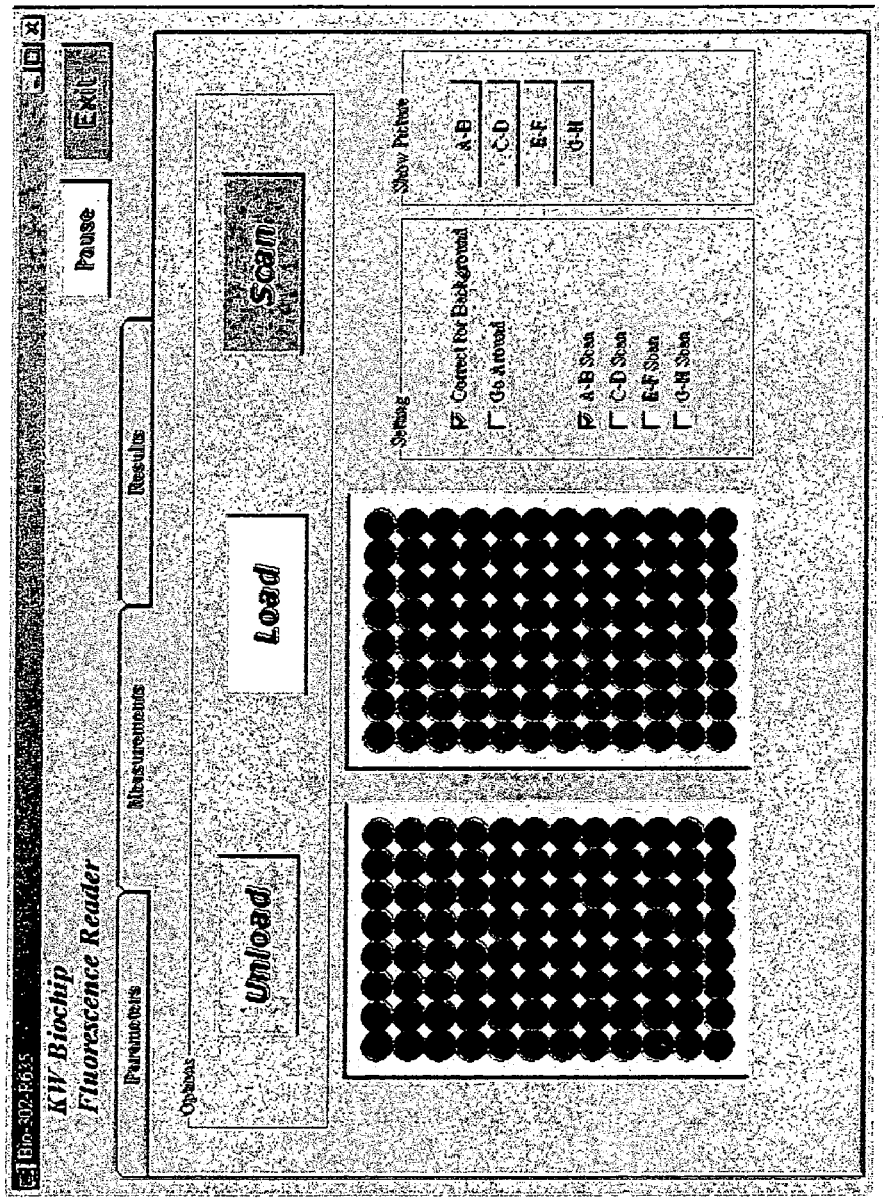
FIG. 6 shows image data of samples for comparison obtained by the fluorescent microarray analyzer of the present invention.

In addition, if desired, image data as shown in FIG. 6 could be produced by the transformation from the signal detected by the spectrophotometer. The image data are used for showing the positions of the DNA spots on a biochip. The signal intensity of each sample comes from signals detected by the spectrophotometer directly and therefore no errors arise as what happened in the process of converting an electrical signal into image data in the conventional biochip.

As mentioned above, spectrophotometer is used as the signal detector of the fluorescent microarray analyzer of the present invention. There is no need to set a filter and more accurate signals of fluorescence are obtained. Furthermore, the signal intensity of each sample comes directly from signals detected by the spectrophotometer so that no errors arise as what happened in process of converting an electrical signal into image data in the conventional biochip. Also, it allows doing a real-time analysis without scanning all samples on the biochip

What is claimed is:

1. A fluorescent microarray analyzer comprising:
   a light source for emitting a light beam;
   a light processing unit for focusing unfiltered light beam onto a biochip and exciting fluorescent targets on the biochip to produce fluorescence;
   a focusing lens for focusing unfiltered fluorescence onto a spectrophotometer;
   a spectrophotometer for detecting signal of the fluorescence; and
   an output device for directly outputting/displaying the signal detected by the spectrophotometer.

2. The fluorescent microarray analyzer according to claim 1, wherein the light processing unit comprises: a beam splitter for redirecting the light bean through a focusing lens which focuses the light beam onto the biochip and exciting the fluorescent targets on the biochip to produce fluorescence.

3. The fluorescent microarray analyzer according to claim 2, wherein the light processing unit further comprises a focusing lens between the light source and the beam splitter to enhance the focusing effect.

4. The fluorescent microarray analyzer according to claim 1 further comprising a platform for holding the biochip and selectively moving in two different directions.

5. The fluorescent microarray analyzer according to claim 4 further comprising a computer comprising at least one set of parameters for controlling the directions of movement of the platform.

6. The fluorescent microarray analyzer according to claim 5, wherein the computer comprises at least one set of parameters for selectively outputting/displaying the signal detected by the spectrophotometer.

7. The fluorescent microarray analyzer according to claim 6, wherein the computer comprises at least one set of parameters for converting the signal detected by the spectrophotometer into image data.

8. A fluorescent microarray analyzer comprising:
   a light source for emitting a light beam;
   a beam splitter for redirecting the light beam through a first focusing lens, which focuses the redirected and unfiltered light beam onto the biochip and excites fluorescent targets on the biochip to produce fluorescence;

a second focusing lens for focusing unfiltered fluorescence on a spectrophotometer;

a spectrophotometer for detecting signal of the fluorescence; and an output device for directly outputting or showing the signal detected by the spectrophotometer.

9. The fluorescent microarray analyzer according to claim 8 further comprising a focusing lens between the light source and the beam splitter to enhance the focusing effect.

10. The fluorescent microarray analyzer according to claim 8 further comprising a platform for holding the biochip and selectively moving in two different directions.

11. The fluorescent microarray analyzer according to claim 8 further comprising a computer comprising at least one set of parameters for controlling the directions of movement of the platform.

12. The fluorescent microarray analyzer according to claim 11, wherein the computer comprises at least one set of parameters for selectively outputting/displaying the signal detected by the spectrophotometer.

13. The fluorescent microarray analyzer according to claim 12, wherein the computer comprises at least one set of parameters for converting the signal detected by the spectrophotometer into image data.

* * * * *